United States Patent
Stirnberg et al.

(10) Patent No.: US 6,941,230 B1
(45) Date of Patent: Sep. 6, 2005

(54) METHOD OF DETERMINING THE GAS QUALITY

(75) Inventors: Dieter Stirnberg, Dortmund (DE); Joachim Kastner, Dortmund (DE)

(73) Assignee: Flowcomp Systemtechnik GmbH, Dortmund (DE)

(*) Notice: Subject to any disclaimer, the term of this patent is extended or adjusted under 35 U.S.C. 154(b) by 0 days.

(21) Appl. No.: 09/869,782

(22) PCT Filed: Jan. 4, 2000

(86) PCT No.: PCT/DE00/00067

§ 371 (c)(1),
(2), (4) Date: Jul. 5, 2001

(87) PCT Pub. No.: WO00/40948

PCT Pub. Date: Jul. 13, 2000

(30) Foreign Application Priority Data

Jan. 5, 1999 (DE) .......................... 199 00 129

(51) Int. Cl.[7] .............................................. G01N 21/00
(52) U.S. Cl. ............................. 702/28; 702/30; 702/32; 702/24; 73/23.2
(58) Field of Search .............................. 702/28, 22–24, 702/27, 30–32, 49, 66, 70, 76, 81, 190, 183, 189, FOR 108, FOR 110, FOR 115–FOR 118, FOR 131, FOR 134, FOR 137, FOR 143, FOR 170, FOR 172; 73/23.2, 23.22, 23.27, 23.28, 23.29, 23.35, 23.37; 422/83, 89; 350/330, 338.5, 334.07, 339.08, 334.13, 341.2, 343; 356/302, 303, 437, 438, 439

(56) References Cited

U.S. PATENT DOCUMENTS

| | | | |
|---|---|---|---|
| 3,950,101 A | 4/1976 | Dewey, Jr. .................. 356/51 |
| 4,594,510 A | 6/1986 | Brown et al. .......... 250/339.13 |
| 4,958,076 A | 9/1990 | Bonne et al. ................ 250/343 |
| 5,237,852 A | * 8/1993 | Kolpak ........................ 73/23.2 |
| 5,822,058 A | 10/1998 | Adler-Golden et al. ..... 336/303 |
| 5,932,793 A | * 8/1999 | Dayton et al. ............. 73/24.05 |
| 6,157,455 A | * 12/2000 | Pinvidic et al. ............. 356/437 |

FOREIGN PATENT DOCUMENTS

| | | |
|---|---|---|
| EP | 0 447 931 | 3/1991 |
| EP | 0 708 323 | 4/1995 |
| EP | 0 708 323 | 4/1996 |
| GB | 2 080 947 A | 7/1981 |
| GB | 2 163 251 | 2/1986 |

OTHER PUBLICATIONS

ISO 12213–1 Natural Gas—Calculation of Compression Factor

Buonanno et al. (1998) "The influence of Reference Condition Correction on Natural Gas Flow Measurement" *Measurement*, Institute of Measurement and Control, Vol 23, pp. 77–91.(no month).

* cited by examiner

*Primary Examiner*—Hal Wachsman
(74) *Attorney, Agent, or Firm*—Collard & Roe, P.C.

(57) ABSTRACT

The invention relates to a method of determining mainly the compressibility number K, the standard volumetric gross calorific value $H_{v,n}$ and the standard density $\rho_n$ of test gases using values determined from a spectrum of the test gases. The invention describes various approaches of translating the values for determining the desired values using the data of the spectrum in the operational condition to the standard reference condition using two-step iteration processes without having to subject the test gases to time-consuming treatments. The invention further relates to devices for determining the values required for the methods and which further develop devices for carrying out the methods.

22 Claims, 11 Drawing Sheets

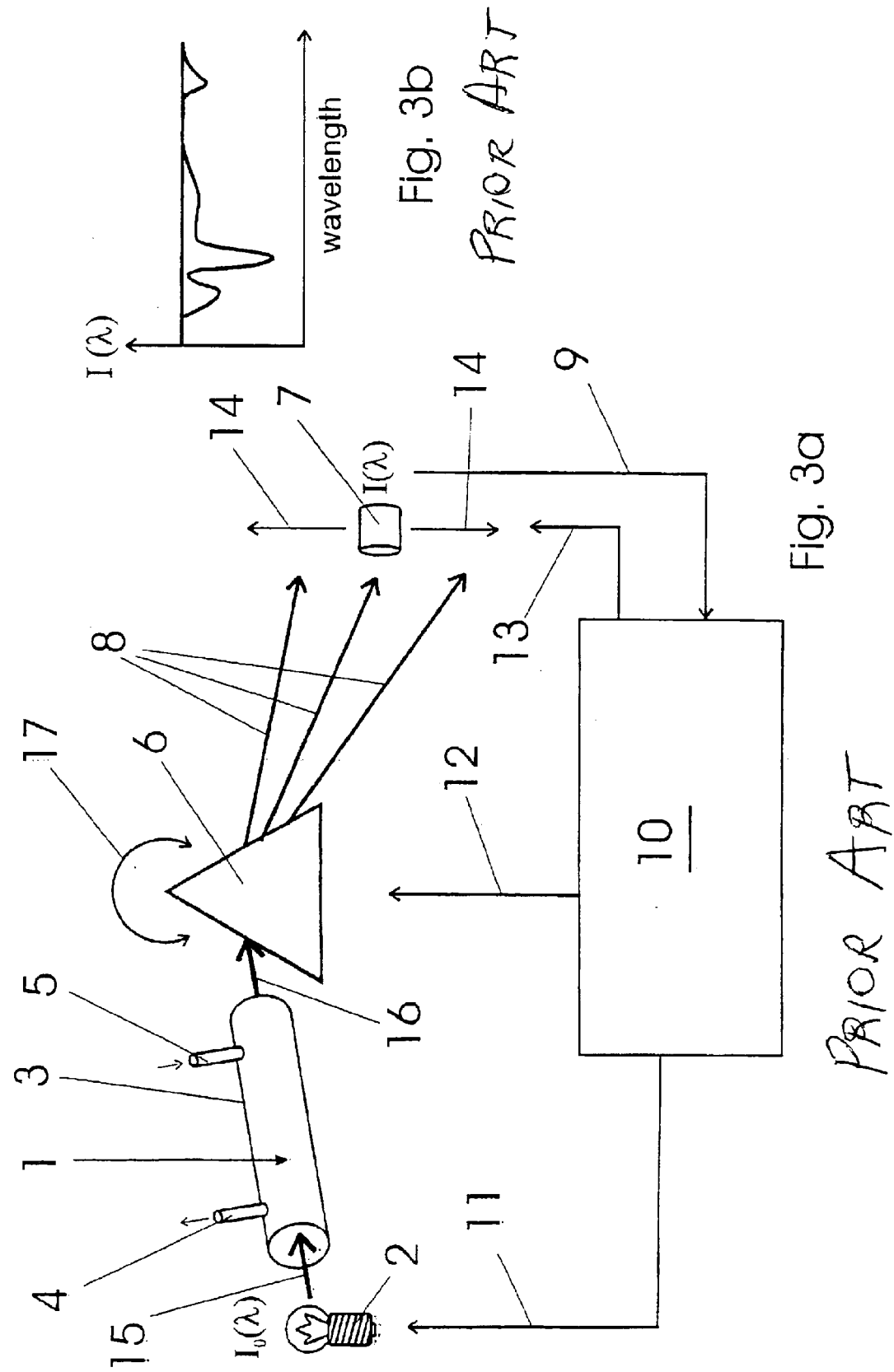

METHOD OF DETERMINING THE GAS QUALITY

CROSS REFERENCE TO RELATED APPLICATIONS

Applicants claim priority under 35 U.S.C. §119 of the German Application No. 199 00 129.4 filed Jan. 4, 1999.

BACKGROUND OF THE INVENTION

1. Field of the Invention

The invention concerns to a procedure for the photometric determination of the quality of gas, particularly of burnable gases, and also devices for the photometric determination of the quality of gas, particularly of burnable gases.

2. The Prior Art

For the registration of the quality of gas for example in distribution networks for natural gas or the same already for a long time devices for the registration of the quality of the guided through gases are used, so-called devices for measuring the condition of gas. Natural gas shows because of being a natural product according to its origin and by mixture respective fluctuations in respect of its composition, whereas the composition for example of natural gas coming from the different hydrocarbons determines essentially the calorific value and there from extrapolated quantities. Therefore it is of great importance for the account of the guided-through amount of gas in a gas supply network and therewith the respective amount of energy, to determine exact the respective condition at the feeding point into the natural gas network and at the deliverance points of the customers and therewith to deduct a definite transported or supplied amount of energy. In doing so for the customer of the gas an invoice can always be stated according of the actual supplied amount of energy regarding to different conditions of the gas and a correspondingly varying amount of energy. Vice versa the detection of the condition of the gas offers the guarantee for the customer, to checkably obtain a desired quality and therewith a required amount of energy.

The registration of the quality of gas obtains additional relevance, since with the drop of the guiding-through monopoly the suppliers of natural gas guide through the same network for delivering gases of quite different provenance and therefore also different composition. Only an as far as possible easy and cost-effective detection of the condition of the gas by means of corresponding disposed cost-effective measuring devices and methods of measurement allows therefore a controllable and accurate accounting.

For the registration of the quality of gas as relevant quantities the standard volumetric gross calorific value Hv.n, the standard density $\rho_n$ and the compressibility coefficient K have to be determined as correct as possible and also regarding the different gas qualities.

In practice for the energetic settlement of accounts first of all by means of flow measuring devices the transported volume Vb of the gas at working conditions (pressure $\rho b$, temperature $T_b$) is measured. With knowledge of the condition of the gas the compressibility coefficient K can be determined, with which the volume of the gas $V_n$ at standard conditions (pressure $\rho_n$, temperature Tn) is calculated.

$$Vn = \frac{\rho_b}{\rho_n} \frac{T_n}{T_b} \frac{1}{K} V_b$$

By means of multiplication of this standard volume with the volumetric gross calorific value $H_{v,n}$ at standard conditions the transported amount of energy Q can be obtained:

$$Q = V_n H_{v,n}$$

Alternative the volume at working conditions vb can directly be multiplied with the volumetric gross calorific $H_{v,b}$ at working conditions (Energymeter).

Another important quantity for applications with natural gas is the thermal output of gas burners; this varies in accordance to the gas quality and is characterised by means of the so-called Wobbe index $W_v$: gases with the same Wobbe index $W_v$ deliver the same thermal output at a burner nozzle. For calculating the Wobbe index $W_v$ the standard density $\rho_n$ of the gas is required, from which the relative density according to air is determined ($d_v$=pgas/pair)

$$W_v = \frac{H_v}{\sqrt{d_v}}$$

Therefore the determination of the gross calorific value $H_{v,n}$ at standard conditions has central relevance for the practical determination of the quality of gas for example for accounting purposes.

Until now different devices for the registration of the gas quality are used. So-called direct and so-called indirect procedures are known. By using direct procedures the quantities to be determine dare measured separately and therefore the gas is transformed to standard conditions, by which partially expensive treatments of the gas are required.

At the most easiest way the gas condition can be determined by means of so-called calorimeters, in which by means of an open flame a gas probe is burnt and out the arising and to a cooling medium submitted heat quantity and the thereupon detectable temperature rise of a cooling medium the calorific value of the burnt gases can be determined. Such devices will need a complicated mechanic for the adjustment of a certain quantitive proportion of gas, combustion air and for example cooling air as cooling medium and are therefore expensive and error prone, especially relating to the open burning enhanced security requirements for the devices are necessary. Also the maintenance and calibration has to be carried out by qualified personnel, beyond that the calorimeter must be used in conditioned rooms. Therefore, the purchase and operating costs of such test assemblies are very high.

Using calorimetry by means of catalytic burning (for example with pellistors) the probe gas is mixed with air and burnt at the 400 to 500° C. hot helixes of a catalyst. The temperature rise of the catalyst is about proportional to calorific value. Because this procedure is based on a sensitive surface effect, it is subject strongish drifts and necessitates frequently calibration with search gas. The catalytic calorimeter are most favorable of all here presented procedures, however they are better suited for control than for accounting) because of their accuracy.

The direct measurement of the density Pb at working conditions is done in one way with hydrostatic balances, very expensive precision devices, with which the buoyancy of a ball filled with nitrogen is measured in accordance to the density of the surrounding medium, here of the probe gas.

With another procedure a thin-walled metal cylinder, which is positioned by a current linkage of the probe gas, is set in oscillation. The density of the surrounding gas determines the resonant frequency of the cylinder, which is captured as sensitive measured quantity. Both procedures are very expensive for the determination of the standard density, because you they require an adjustment to the standard conditions.

The compressibility coefficient K can in this way not be measured directly, instead can be calculated by means of different numerical standard-arithmetic techniques out of the directly measurable gas quantities. One of these procedures, the so-called GERG88-procedure (DVGW-worksheet 486) needs thereby the input quantities listed in table 1. The amount of substance of $CO_2$ is determined according to the today's state of the art by a non dispersive infrared-spectroscopical procedure (NDIR), whereby the gas must be brought into a defined condition near or at standard conditions. The amount of substance of $H_2$ is practically of significance only when working with coke oven gases and can be practically left unattended in the typical natural gases today distributed in Europe. The compressibility coefficient K can be determined to $10^{-3}$ with the help of the GERG88-equation in case of sufficient accuracy of the input quantities.

TABLE 1 input quantities of the GERG88-procedure

| | |
|---|---|
| Pb | pressure at working conditions |
| Tb | temperature at working conditions |
| $\rho_n$ | density at standard conditions |
| $H_v$, n | volumetric gross calorific at standard conditions |
| $XCO_2$ | amount of substance of $CO_2$ |
| $xh_2$ | amount of substance of $H_2$ |

The other procedure for determination of the behaviour of real gases is done according to the AGA8-92DC-equation equation (ISO 12213-2:1997 (E)). This process requires as input quantities the amount of substance of 21 leading gas components (table 2) and gains just as an accuracy of $10^{-3}$.

TABLE 2 input quantities of the AGA8-92DC-equation

| | |
|---|---|
| methane | $CO_2$ |
| ethane | $N_2$ |
| propane | $H_2S$ |
| isobutane | He |
| n-butane | $H_2O$ |
| isopentane | $O_2$ |
| n-pentane | Ar |
| n-hexane | $H_2$ |
| n-heptane | CO |
| n-octane | pressure |
| n-nonane | temperature |
| n-decyl hydride | |

The state of the technology includes besides the direct measurement techniques also the indirect measurement of the gas quality by means of gas chromatography. Thereby a defined volume of the probe gas is brought into a defined condition and is carried by a carrier gas, typically helium, through a system of gaschrornatographic separation columns. On account of their different times of retention the individual gas components reach the downstream sensor, generally this is a detector for caloric conductibility, at the end of the separation column separated in time. The peak area of the sensor signal can therefore be interpreted as amount of substance, whereas the evaluation must be carried out in comparison with a reference gas, that must have just about a similar composition like the probe gas. The drawback of the gas chromatography has its reason in the expensive sample preparation and installation of the whole system, and in the expensive maintenance and operation by well-trained personnel. From the amounts of substances of the individual gas components, as the gas chromatography delivers, all relevant gas quantities can be calculated. For the implementation of such indirect measurements in the way of chromatography automatically working process chromatographs with detectors for caloric conductibility are deployed. These devices measure normally eleven components of the natural as ($N_2$, $CO_2$, $CH_4$, $C_2H_6$, $C_3H_8$, $C_4H_{10}$, $C_5H_{12}$, $C_6+$ and so on). As carrier gas helium will be used, whereby its light volatility in practice often leads to prematurely emptying of the bottle for the carrier gas and therefore leads to short maintenance cycles for such a device for measuring the quality of a gas. As calibrating gas a gas is chosen, that is similar to the natural gas to measure. Such chromatographic systems carry out measurement cycles without interruption, in order for capturing changes in the quality of the gas immediately. These leads to a high consumption of carrier gas and calibrating gas and has moreover the effect, that maintenances of the device have to be performed in relatively short intervals.

It is also known, to determine the composition of a gas with conventional infra-red-gas-analyzers. Such analysers working in the middle infra-red or near infra-red area offer however not the requested requirements to high precision and in particular to stability for a determination of the caloric value under the measurement conditions which are required here. Also always a parallel reference measurement is to be carried out beside the intrinsic measurement of the probe gas, for the sake of compensating the at least essential influences of failures. As a measuring result the known infra-red-gas analysers deliver superimposed frequency spectrums, that make very difficult a conclusion to individual components of a inspected gases, if not even forbid such a conclusion.

In the literature also has been described a infrared spectroscopical procedure for gas analysis ("Optical BTU sensor Development", Gas Research Institute GRI-93/0083), that determines by means of so-called multivariate analysis (MVA) of the near infrared spectrum of gases the volumetric concentration of the amount of substances of the containing carbon components of the gas and therewith of the volumetric calorific value under operating conditions. This procedure delivers however not the calorific value $H_{v,n}$ under standard conditions and not the standard reference density $\rho_n$ and the amount of substance Of $CO_2$, so that it is not qualified for the determination of the compressibility coefficient K and therefore not for the complete determination of the quality of a gas. By the determination of the calorific value by means of known photometric methods moreover minor claim to the necessary instrumental equipment for the realisation of the procedures are required, whereby a benefit in the speed of the coverage of the absorption spectrums of the natural gas in near or middle infrared spectral area is obtained. The entire absorption spectrum of the natural gas is therefore put additive together from of the sum of single spectrums of components represented in gas and therefore can be measured and be analysed with the aid of more appropriate methods of spectral analysis. Doing this the ascertained quota of extinction of a component in the entire spectrum of the natural gas is in effect equivalent to the part of the concentration of this component within search gas (so-called Beer-Lambert-law). With the knowledge of the calorific value of this respective component the calorific value of the entire mixture of gases can then be calculated as a summation value. Problematically in this procedure of spectral analysis is however the intense overlap by absorption bands of different components, which frequently lead to inaccurate results and beyond that to a high calculation effort.

One more infrared spectroscopical procedure concerning to the DE 198 38 301 Al will act as a direct spectral evaluation (DSA) with a spectral function, with which the spectrum of the gas is folded. The procedure allows the specification of the volumetric calorific value $H_{v,n}$ under operating conditions direct from the spectrum. Herewith it is utilized, that while burning the gas the respectively caused heat of the reaction is based on the combustion of C-H-bindings and a thereby caused heat quantity depends to the present binding energy. This is thereby exploited, that the oscillations of the C-H-bindings, which show an equal to each other, certain binding energy and produce the same heat quantity during a combustion, interact with an associated wavelength of an electromagnetic radiation. Hereby it is possible by means of a wavelengths-resolved measuring and a wavelengths-dependent valence of the grade of interaction of these oscillations to calculate the calorific value $H_{v,b}$ of the gas, without the requirement of an identification of individual gas components. In this document it is additionally proposed a device for the realisation of such a procedure, which is tuned for the specific requirements of the measuring method and enables a weighted summing up of the grades of interaction. With this procedure indeed the calorific value $H_{v,b}$ of a mixture of gases under operating conditions can be determined, the other quantities relating to the determination of gas quality can itself not be determined with measuring techniques.

In the publication of G. Buonanno et al. "The influence of reference conditon correction on natural gas flow Measurement" in the British magazine "Measurement" vol. 23, No. 2 dated $1^{st}$ Mar. 1998 (published of the Institute of Measurement and Control, London) on the pages 79–81 is indicated a procedure for determination on the conversion of gas volumes, in which the compressibility factor Z is determined iterational according to the procedure SGERG-88 und afterwards the parameters $\epsilon$ and $\chi$ are calculated. These parameters are mathematically directly connected with the input quantities pressure p, temperature T an the amounts of substances.

Further in the U.S. Pat. No. 4,958,076 and the U.S. Pat. No. 5,822,058 photometric devices with filtering units are known.

After having today's state of the art there is no, especially no uniform procedure, that determines under operating conditions the substantial quantities volumetric standard-calorific value $H_{v,n}$, standard-density $\rho_n$ and compressibility factor K.

SUMMARY OF THE INVENTION

Therefore it is object of the pending invention, to propose procedures and devices for the determination of the quality of gas, with which the substantial quantities volumetric standard-calorific value $H_{v,n}$, standard density $\rho_n$ and compressibility factor K can be determined by means of a spectroscopical registration of the quality of the gas as well as respective evaluations.

The solution of the object according to the invention results in respect of the procedures in accordance with the features of the process of the invention. The solution of the object according to the invention results in respect of the devices in accordance with the features of the device of the invention.

The invention concerns a first procedure with which the determination of the quality of gas of a probe gas, in particular a burnable gas, is carried out based on a spectrum of the probe gas determined under operating conditions by means of infrared spectroscopical measurement procedures. Herein the quality of gas of a probe gas is determined in such a way according to the invention, that in a first step of the procedure the amounts of substances xi of the components of the probe gas at operating conditions are determined out of the spectrum, where after default values for compressibility factor K and real gas factor $Z_n$ are preset for calculation of the wanted compressibility factor K and than out of quantities at operating conditions of the probe gas as well as from the amounts of substances xi and substance specific quantities such as calorific values per sort of molecule of the components and the respective masses of molecules, and taking into account of the selected default values for compressibility factor K and real gas factor $Z_n$ the needed input quantities for the determination of the compressibility factor K are determined. These input quantities are used, to calculate the compressibility factor K by means of standard-arithmetic procedures. In a further step of the procedure an iterative calculation in the way of an iterative recalculation of the input quantities is carried out with the determined value for the compressibility factor K as long, until the value of the compressibility factor K converges. There from the volumetric standard calorific value $H_{v,n}$ and the standard density $\rho_n$ can be calculated. In the case of converging the needed quantities compressibility factor K, standard calorific value $H_{v,n}$ and the standard density $\rho_n$ for determination of the quality of gas of a probe gas are known and can be used respectively for example for the calculation of the energy content of the transported gas. At each iteration the just determined value for the compressibility factor K is put back again into the equations for calculating the input quantities of the standard-arithmetic procedure and a new iteration step is carried out. By means of this procedure starting with the determination of the amounts of substances $x_i$ out of the recorded spectrum and the iteration procedure with the help of the default values for the compressibility factor K and real gas factor $Z_n$, after a respective number of iteration steps the really existing values for the compressibility factor K and there from than the values for standard-calorific value $H_{v,n}$ and the standard density $\rho_n$ in the probe gas can be determined with adequate accuracy. In this way the compressibility factor K is determined out of the spectroscopical measurable quantities in operation conditions as well as out of the default values for the compressibility factor K and real gas factor $Z_n$, and the real gas calculation itself can be carried out with standard-arithmetic procedures and these arithmetic. procedures itself are again iterational procedures.

Therefore there is a base of a two-stage iteration, in which in a first iterational step with the default values for the compressibility factor K and real gas factor $Z_n$ and the input quantities of the standard-arithmetic procedure the compressibility factor K is calculated by means of iterational procedures and in the case of non-convergence the compressibility factor K and the quantities, which can be determined again there from, are put back after a new calculation of the input quantities of the standard-arithmetic procedure as input quantities for a new iterational loop. Beneath the convergence of the compressibility factor K the convergence of the standard-calorific value $H_{v,n}$, and the standard density $\rho_n$ can be proofed. This procedure owns the advantage, that out of the quantities being measurable at operating conditions and the spectrum, which can be determined direct at the operating conditions, the standard values of the probe gas can be determined directly without subjecting the probe gas to the otherwise necessary, expensive treatments for transferring it into standard conditions.

In an especially preferred embodiment as a standard-arithmetic procedure for the determination of method of iteration AGA8-92DC is used, which is commited as an international uniform arithmetic procedure in ISO 12213/2. As significant input quantity for this procedure AGA8-92DC here the molar amounts of substances of the infrared active components and the molar amount of substance of nitrogen $N_2$ is used.

In an other preferred embodiment as a standard-arithmetic procedure for the determination of the compressibility factor K the method of iteration GERG88 is used, which is commited in the DVGW-working sheet 486 and described detailed. This method of iteration allows also the determination of the compressibility factor K, wherein as input quantities out of the molar amounts of substances of the infrared active components the standard-calorific value $H_{v,n}$, and the standard density $\rho_n$, and the concentration of $CO_2$ can be calculated.

In an especially preferred embodiment the determination of the amounts of substances $X_1$ of the infrared active components of the probe gas at operating conditions is carried out starting from the recorded spectrum by means of a procedure according to the multivariate analysis (MVA), which is described in detail in the report of the Gas Research Institute GRI-93/0083 "Optical BTU Sensor Development." By using this procedure of multivariate analysis (MVA) out of the spectrums of the probe gas, recorded at operating conditions, the amounts of substances of the infrared active components are determined and are therefore available for the calculation of the compressibility factor K.

In a preferably embodiment the default values of the compressibility factor K and the real gas factor $Z_n$, are taken from a characteristic diagram, that describes the influence of the pressure $\rho_b$ at operating conditions and the temperature $T_b$ at operating conditions for a known composition of a gas similar to the composition of the probe gas. By doing this the fact is used, that the pressure $\rho_b$ at operating conditions has a great influence, the temperature $T_b$ at operating conditions as also the real composition of the gas, especially for usual compositions of burnable gases, have a minor influence at the values of the real gas factor $Z_n$. Therefore it is possible with characteristic diagrams of a gas similar to the composition of the probe gas, which have been determined before and in which the relation between pressure and temperature is outlined, to take a starting value for the iterative calculation according to a standard-arithmetic procedure as a good first approximation for the pressure $\rho_b$ at operating conditions and the temperature $T_b$ at operating conditions, which converges with a real good accuracy after a small amount of iteration steps to the real compressibility factor K.

Furthermore it is especially preferable, that directly from the recorded spectrum the amounts of substances of the single burnable components of the probe gas at operating conditions and the amount of nitrogen $N_2$ of the probe gas are determined as a function of the amounts of substances of the infrared active components of the probe gas. Therefore as an additional information the pressure of the probe gas, in which the amount of substance of nitrogen is also taken into consideration, has relevance for the calculation.

In further embodiment the amount of substance of nitrogen $N_2$ and the amounts of substances of the infrared active components complements each other resulting in the total volume of the probe gas, in which further substances, as for example oxygen $O_2$, hydrogen $H_2$ and water for example are contained in typical burnable gases only in small traces and therefore can as a rule be neglected.

The invention concerns furthermore to a procedure for the determination of the quality of gas of a probe gas, in particular a burnable gas, proceeding from a spectrum of the probe gas determined under operating conditions by means of infrared spectroscopical measurement procedures.

This procedure will hereby be developed further in a way according to the invention, that in a first step of the procedure default values for compressibility factor K and real gas factor $Z_n$ are preset for calculation of the wanted compressibility factor K, in a further step of the procedure input quantities for the determination of the compressibility factor K are determined by using the pressure $\rho_b$ at operating conditions and the temperature $T_b$ at operating conditions of the probe gas, which can be determined without problems from the operating condition of the probe gas, and out of the values for the calorific value $H_{v,b}$ at operating conditions and the density $\rho_b$ at operating conditions, whereby as further input quantity the molar amount of substance of $CO_2$ is determined by means of a further absorption band of the spectrum. Hereby both the calorific value $H_{v,b}$ at operating conditions as also the density $\rho_b$ at operating conditions can be directly determined based on the spectrum, in which simultaneously based on the same spectrum the further absorption band for the amount of substance of $CO_2$ can be determined. With these input quantities in a further step of the procedure the compressibility factor K is calculated by means of the iterational procedure GERG88. On the base of theses results of the iterational procedure GERG88 than it is examined, if the value for the compressibility factor K converges and than there from the volumetric standard calorific value $H_{v,n}$, the standard density $\rho_n$ and the amount of substance of $CO_2$ is calculated. If a convergence is ascertainable, than as results of the procedure according to the invention the determined compressibility factor K as also the therewith calculated values for the standard calorific value $H_{v,n}$, the standard density $\rho_n$ and the amount of substance of $CO_2$ can be used directly for further purposes. If a convergence is not ascertainable, than an iterative recalculation of the input quantities is carried out with the determined value for the compressibility factor K as long, until the convergence of the compressibility factor K and if necessary the standard calorific value $H_{v,n}$ and the standard density $\rho_n$ is to be noticed. During each iteration the just determined value of the compressibility factor K is put again into the equations for the calculation of the input quantities of the standard-arithmetic procedure and a new iteration step is carried out. The procedure according to the invention shows the advantage, that also without knowledge of the exact amounts of substances of the single components contained in a probe gas the wanted target quantities at working conditions can be solely determined out of the spectroscopical quantities at working conditions and the start values for the compressibility factor K and the real gas factor $Z_n$, in which a two-staged iterational approach, on one hand the calculation by iteration of the compressibility factor K while carrying out the procedure according GERG88, on the other hand with an iteration while recalculating again the input quantities for GERG88 on base of the in the step before determined compressibility factor K until the convergence of the results for the compressibility factor K and the volumetric standard calorific value $H_{v,n}$, and the standard density $\rho_n$ can be carried out. This so-called direct spectral evaluation (DSA) is fundamentally known in the state of the art for the determination of the calorific value $H_{v,b}$, in which the calculation of the density $\rho_b$ at working conditions and the compressibility factor K solely on the base of the recorded spectrum was not known until now.

It is most preferable, that the calorific value $H_{v,b}$, at operating conditions and the density $\rho_b$ at operating conditions can be determined by means of spectral functions for weighting of a value directly from the spectrum of the probe gas, in which for this it can be used, that based on the oscillation frequency of the binding of the infrared active components of the gas their spectral position can be seen and this again relates to the reduced mass of the binding partners. With this the spectrum contains in its amount and its spectral distribution also information for the determination of the density $\rho_b$ at working conditions, if it is suitably evaluated.

In a further embodiment with the spectral functions for weighting of a value the weighted influence of the amounts of substances of the components of the probe gas is described for the calorific value $H_{v,b}$, at operating conditions and the density $\rho_b$ at operating conditions. In this case the single amounts of substances have not to be determined explicitly because of the spectral functions for weighting of a value, but the influence of these amounts of substances is represented in the spectral functions for weighting of a value.

Also it may be thinkable, that the default values for compressibility factor K and real gas factor $Z_n$ are taken from a characteristic diagram, that describes the influence of the pressure $\rho_b$ at operating conditions and the temperature $T_b$ at operating conditions for a known composition of a gas similar to the composition of the probe gas. As described before for the procedure, in this way good starting values as a good first approximation for the compressibility factor K and the real gas factor $Z_n$ can be determined, which contributes to a fast convergence also of this procedure according to the invention.

The invention concerns furthermore a generic photometric device for the determination of a transmission spectrum of a probe gas.

Generic device can be developed further, if the spectral switch unit shows a chopper arrangement, which transmits because of their selective transmission behaviour only specific regions of the spectrum in the measurement radiation caused by the probe gas to the radiation receiver. In this way the chopper arrangement is be provided with an aperture with a spiral opening, in which the release of the regions of the wavelength of the measurement radiation is caused continuously for the whole spectrum. By this means also compositions of probe gases can be determined, whose spectrums have to be captured over wide regions, also a higher flexibility for the evaluation of the spectrums can be obtained by this.

In this way in further development the chopper arrangement can be provided with such a transmission behaviour, that the transmitted spectral regions are suitable for the further evaluation by procedures of the direct spectral evaluation (DSA). By means of the chopper arrangement only that part of the whole spectrum is measured, which is of interest for the determination of the quality of gas for example of a probe gas of typical composition at all regions and with simple mechanical means allows an exact selection of these spectral regions. Also such a chopper arrangement is built up easily and mechanically solid and insensitive.

There is a special advantage, if the released wavelength of the measurement radiation, which passes through the chopper arrangement, can be obtained by means of capturing the rotational position of the aperture. This can be realized in a simple manner for example by a shaft encoder, which is build up mechanically simple, inexpensive and robust and allows a secure synchronisation of the capturing of the spectrums with the respective wavelength.

In a further development the chopper arrangement is provided with two groups of sector elements alternatively releasing the measurement radiation, in which a first optical waveguide guides the measurement radiation released by the sector elements of the first sector element group into the probe cell and after passing through the probe cell to the radiation receiver and a second optical waveguide guides the measurement radiation released by the sector elements of the second sector element group directly to the radiation receiver. At the here especially based application very high requirements are to be fulfilled in respect of the long-time stability of the device against signal drift. The following three factors contributes to a signal drift: fluctuation in respect of the luminous power of the radiation source, fluctuation of the sensitivity of the radiation receiver (both for example as result of aging processes) and fluctuation of the $CO_2$-concentration in the surrounding air, which results in an instable $CO_2$-under underground spectrum. The $CO_2$-concentration in the surrounding air and therewith in the free beam path of a device varies for example on behalf of the presence of persons in the surrounding. All three influences can be compensated by means of the here proposed dual-beam building up of the device, with which a permanent comparison of the signal with the reference signal can be carried out. By means of the sector elements of the sector element groups the each released measurement radiation of that waveguide can be used, which is guided to the radiation receiver, as reference for eliminating the influence of existing CO: in the surrounding of the probe cell and/or the device that changes the radiation source and/or the radiation receiver. Beneath the elimination of the influence of $CO^2$ in the surrounding in this way also changes of the radiation source and/or the radiation receiver can be eliminated, which can be the result of aging processes or contaminations.

In this way in a first embodiment the measurement radiation released by the sector elements of the sector element groups can be concentrated by means of first and second optical waveguide into one or more filters or a dispersive element, preferably a monochromator.

There is a special advantage, if the radiation receiver collects the measurement radiation, which is coming out of the one or more filters or the dispersive element and each released through the sector elements of the sector element groups of both optical waveguides.

In a further embodiment it may be possible, that the measurement radiation, which is each released through the sector elements, is guided through the first and the second waveguide to the input of the one or more filters or the dispersive element, in which at the chopper arrangement also available further sector element groups lock on the measurement radiation, which is released of the one or more filters or the dispersive element, alternatively to the radiation receiver. By theses means a reliable synchronization of the modulations can be assured using a mechanically simple build up arrangement of the sector element groups of the aperture. In a further variant it may be thinkable, that the chopper arrangement carries out both the selection of the wavelengths for the spectrum as well as the alternating reverse of the measured section between the waveguides.

In this case a further development may be possible, in that the measurement radiation, which is each released through the sector elements, is guided together by means of the first and the second waveguide in a Y-fibre coupler, which guides the measurement radiation of the first and the second waveguide to the one or more filters or the dispersive element. This allows an especially simple design of the filter and the dispersive element and the concentration of the splitted beams.

In further development it may also be thinkable, that the probe cell is sweepable with an infrared inactive gas, preferably nitrogen $N_2$, for carrying out a null measurement for the compensation of dirt accumulation or the same of the optical facilities of the device. In this way it is possible to capture with this probe cell filled with gas of definite and known properties, if there are deviations relative to an initial state and these deviations can be taken into consideration for further measurements.

An especially preferred embodiment of the procedures according to the invention and the device according to the invention shows the drawing.

BRIEF DESCRIPTION OF THE DRAWINGS

It is shown in

In FIG. 1 it is described, which distribution can be found in the spectrum for different components contained in natural gas.

Natural gas as distributed typically in Europe consists generally of the components as methane, ethane, propane, butane, pentane and higher hydrocarbons such as carbon dioxide and nitrogen. According to DIN 51857 mixtures of gases count as similar to natural gas, if their amounts of substances fulfil the following conditions:

TABLE 3 limiting value for gases similar to natural gas

X(CH4) >= 0.5
X(N2) <= 0.3
X(CO2) <= O. I S
x(C2H6) <= 0.15
7-xi over all other components <= 0.05 according to DIN 51587

The remaining components are mostly higher hydrocarbons with amounts of substances of about $10^{-3}$, further substances as $O_2$, $H_2$, water and other occur in typical natural gases in trace amounts, which do not disturb a measurement with the demanded accuracy. With exception to nitrogen all relevant components of mixtures of gases similar to natural gas are infrared active, so that they absorb radiation in the infrared spectral region and can be detected in this way.

Figure 1:
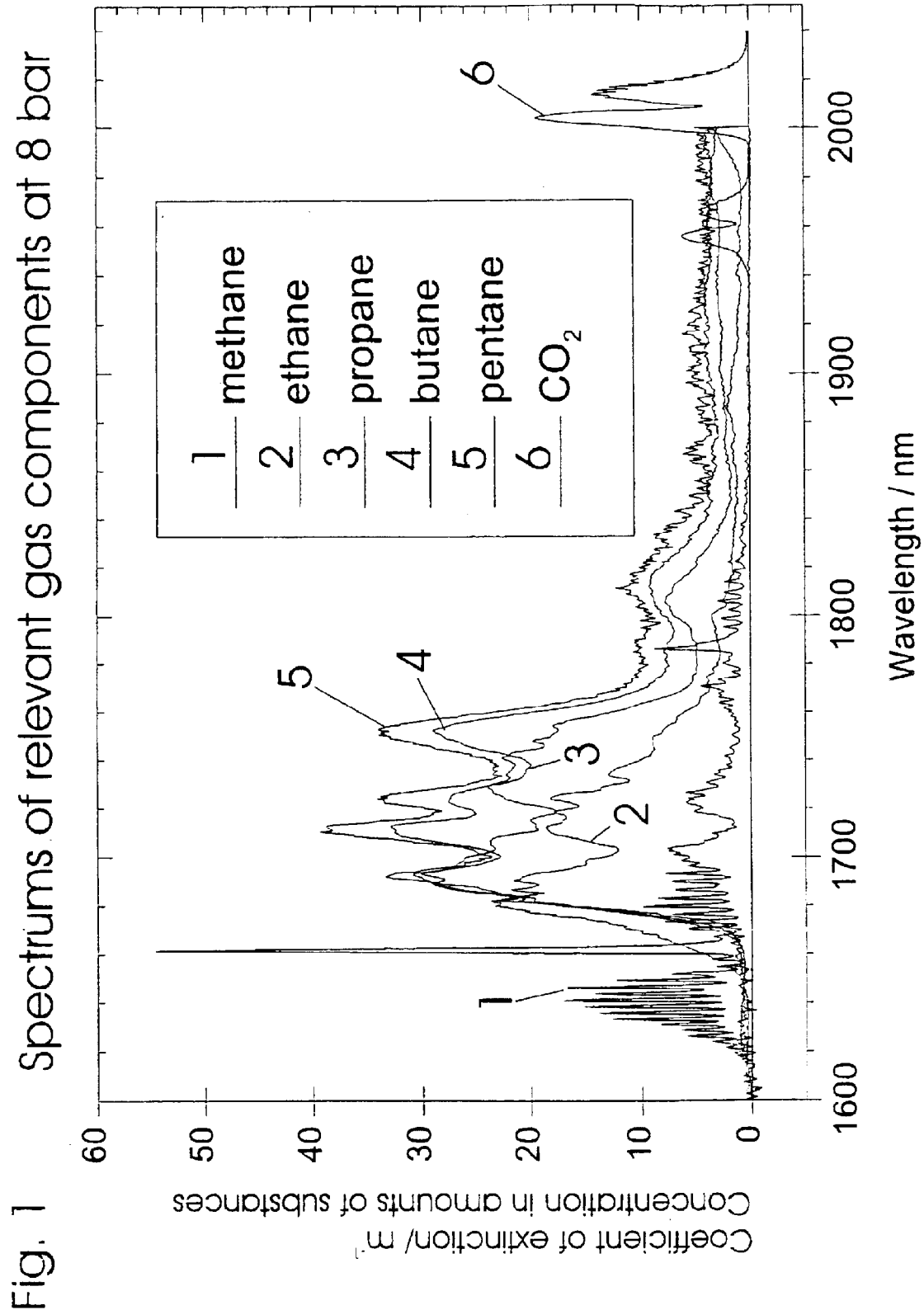
FIG. 1—a typical distribution in a spectrum for different ingredients of natural gas, FIG. 2a—fundamental procedure of a two-staged iterational procedure, FIG. 2b—fundamental procedure of a two-staged iterational procedure, FIG. 3a—a fundamental structure of a and 3b photometric device according to the state of the art, FIG. 4—a device according to the invention, which is coupled to a probe cell by means of waveguides and determines the spectrums by means of filters, FIG. 5—a first device according to the invention, in which a chopper arrangement with a sector element aperture is provided for selection of wavelengths, FIG. 6—a second device according to the invention, in which a chopper arrangement with a spiral aperture is provided for selection of wavelengths, FIG. 7—a further device according to the invention according to the reference beam principal, FIG. 8—an embodiment of the device according to FIG. 7 with synchronisation by the chopper arrangement itself, FIG. 9—an embodiment of the probe cell as hollow shaft guide, FIG. 10a—a connection of the probe cell to a waveguide and 10b with the help of GRIND-lenses, FIG. 11—an embodiment of the invention with a modulation of the measurement radiation.

The extinction coefficients of the relevant gas components are described in FIG. 1, while the components methane and $CO_2$ are isolated in specific spectral regions, the higher hydrocarbons overlap spectral very much. The FIG. 1 shows moreover typical spectral regions for the determination of the single components ($CH_4$, $CO_2$) respectively groups of components ($C_2H_6$ and higher hydrocarbons).

According to the Beer-Lambert-law the infrared components contribute to the extinction in the infrared spectrum according to their particle number density in the optical measuring volume. Based on the spectrum the volumetric amounts of substances of the infrared substances of an unknown gas probe can be determined at measuring respective working conditions.

For determining the volumetric calorific value at working conditions these information are sufficient, because the "invisible" nitrogen does not contribute to the calorific value. According to the state of the art for this two procedures are described. According to the one procedure (DVGW-working sheet 486) the analyses of the gas mixture is carried out referring to their composition of single components. Therefore the amounts of substances of the single burnable components are determined out of the spectrums by means of the mathematical procedure of multivariate analyses (MVA) and the calorific value is calculated as corresponding weighted sum. In the second procedure(direct spectral analyses DSA) (ISO 12213-2:1997(E)) not single components are identified, but by means of a convolution integral with a specific spectral function the calorific value at working conditions is calculated directly out of the spectrum.

In practice the measurement of the quality of gas not only the calorific value $H_{v,n}$ at operation conditions is expected, but the calorific value $H_{v,n}$ at standard conditions and the standard density $\rho_n$ and the compressibility factor K. For the calculation of these quantities the knowledge about the amount of substance of nitrogen in the gas is required, but this cannot be gained directly out of the infrared spectrum.

The procedures introduced here make possible a determination of the relevant gas quantities out of the infrared spectrum without explicit knowledge of the amount of substance of nitrogen. Thereby the contribution of nitrogen is printed out as function of the other spectroscopical measurable components; as additional information supplementary the pressure of the gas enters the figure, which also takes into account the amount of substance of nitrogen. Basis for this is the gas equation of the real gas with the pressure p, the volume V, the real gas factor Z as function of the condition (p,T) and the composition of gas $x_i$, of the sum of all the molecules N, the Boltzmann factor $k_B$ and of the temperature T.

$$p\ V = Z(p,T,X_i) N\ k_B T$$

With this the mathematical representations of the wanted quantities for a first procedure for the determination of the compressibility factor K result in the following equations. These representations contain however the wanted compressibility coefficient K as well as the unknown real gas factor $Z_n = Z(\rho_n, T_n)$ of the unknown gas at standard conditions.

The calculation is achieved by one in FIG. 2 nearer explained two-stage iterational approach in which the appropriate starting values for K and $Z_n$ are selected. For the determination of the compressibility factor K either the procedure GERG88 (DVGW-worksheet 486) or the procedure AGA-92DC (ISO 12213-2:1997(E)) will be used. The respective input quantities of the two iterational procedures are calculated out of the spectrum analysis of the gases with the applicable selected starting values for $Z_n$, and K.

The input quantities for the standard-arithmetic procedure AGA8-92DC are described with the volumetric concentrations of the amounts of substances of the infrared active components and the starting values for K and Zn as following:

$$X_i = \frac{k_b T_b}{p_b V_n} K Z_n N_i$$

$$X_{N2} = 1 - \frac{k_b T_b}{p_b V_b} K Z \sum_{n_1} N_i$$

Herein the $x_i$ indicate the amounts of substances of the infrared active components and XN2 the amount of substance of nitrogen.

The input quantities for the alternative standard-arithmetic procedure GERG88 are calculated with the volumetric concentrations of the amounts of substances of the infrared active components and are described with the starting values for K and Zn as follows:

$$H_{v,n} = \frac{p_n T_b}{p_b T_n} K \sum_i H_{m,i} N_i$$

$$p_n = \frac{p_n T_b}{V_b p_b T_n} K \sum (m_i - m_{N_2}) N_i + \frac{p_n m_{N_2}}{T_n k a Z_n}$$

$$x_{CO2} = \frac{k a T_b}{p_b V_b} K\ Z_n N_{CO_2}$$

with calorific values $H_{m,i}$ per molecule of the component i and the respective masses of molecules $m_i$, the mass of the molecule of nitrogen $mN_2$ and the number of $CO_2$-molekules $NCO_2$ in the measurement volume.

A multivariate analysis (MVA), as outlined in the literature (DVGW-worksheet 486), delivers the volumetric amounts of substances of the gas components at operation conditions. The here presented procedure describes, how moreover with these data the standard calorific value $H_{v,n}$, the standard density $\rho_n$ and the compressibility factor K can be ascertained.

With the procedure by means of a spectral weighting function can be evaluated the spectrums directly without detailed resolution of the individual gas components. The specification of the calorific value $H_{v,b}$, at operation conditions according to this procedure is lined out in the patent application DE 198 38 301.0. The volumetric amount of substance of $CO_2$ at operating conditions can be evaluated as separate absorption band according to common spectroscopic procedures.

Vital component of the here introduced procedure is the spectral measurement of the density $P_b$ at working conditions, therefore also the convolution of the spectrum with a spectral function is used. The physical background of the procedure is herein, that each binding of the infrared active gas components contribute for extinction and so represents the mass of the partners of the binding in the spectrum. The frequency of oscillation of the binding and therewith their spectral location depends on the reduced mass of the partners of the binding. Therewith the spectrum contains in its amount and its spectral distribution at appropriate evaluation information for the determination of the density of the gas.

The input quantities for the herein used standard-arithmetic procedure GERG88 result thereby out of the direct evaluation of the spectrums and with the starting values for K and $Z_n$:

$$H_{v,n} = \frac{p_n T_b}{p_b T_n} K H_{v,b}$$

$$\rho_{v,n} = \frac{p_n T_b}{p_b T_n} K \rho_{v,b}$$

$$X_{CO_2} = \frac{k a T_b}{p_b V_b} K Z_n N_{CO_2}$$

Figure 2B:
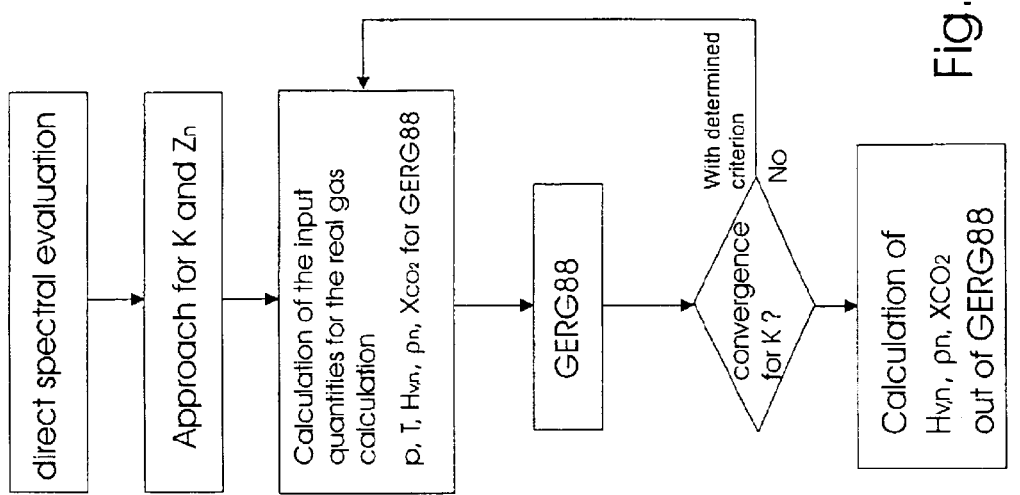
Figure 2A:
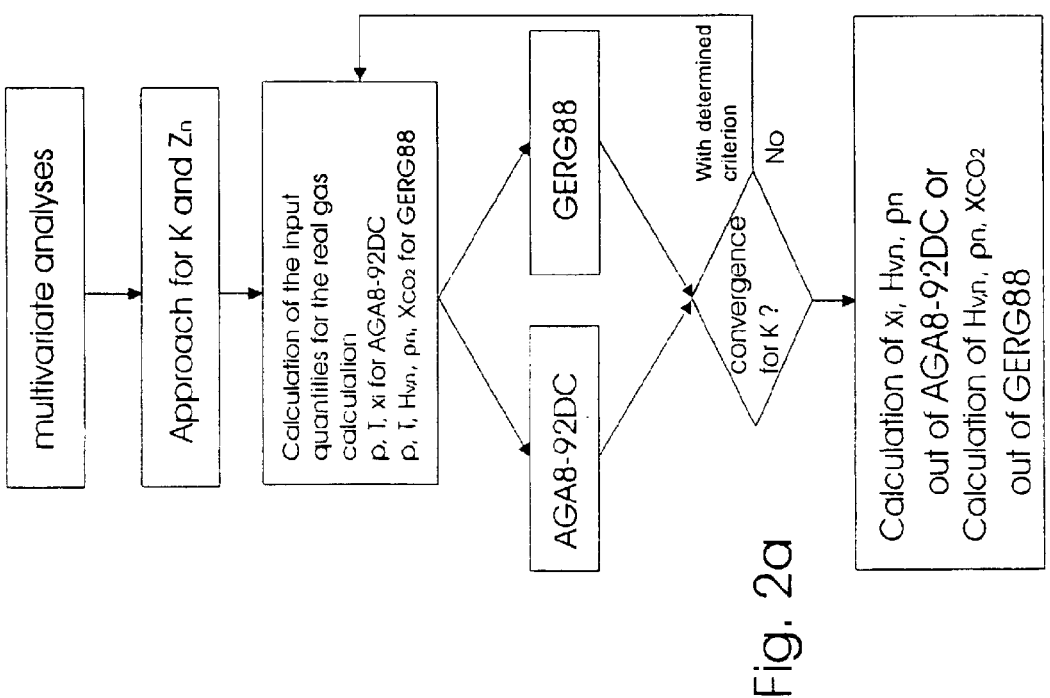

In the FIGS. 2a and 2b the flows of the two-stage iterational procedure according to the above mentioned equations are illustrated once more precisely. In the FIG. 2a is represented the principal flow of the calculation of the procedure with the both alternative iterational procedures AGA8-92DC and GERG88, which start from the results of the multivariate analysis (MVA) by means of the ascertained spectrum. In the FIG. 2b is represented however the principal flow of the calculation of the procedure that starts from the results of the direct spectral evaluation (DAS) and than uses the iterational procedure GERG88.

At the procedures according to FIG. 2a a first approach for the values of K and $Z_n$ is made, according to the determination of the directly with conventional means measurable quantities of the probe gas as pressure $\rho_b$ and temperature $T_b$, at operating conditions as well as of the evaluation of the spectrum by means of the multivariate analysis (MVA), which at most easy can be drawn from a characteristic diagram, that represents the influence of pressure $\rho_b$ at operating conditions and temperature $T_b$ at operation condition for a known composition of gas similar to the probe gas. With these quantities then for the first time—according to a chosen standard-arithmetic procedure (AGA8-92DC or GERG88) the respective input quantities of the respective standard-calculation procedure will be calculated and these are then used in the respective iterational procedure of the standard-arithmetic procedure. As a result of this a value for the compressibility factor K is obtained as well as the here from calculatable quantities standard calorific value $H_{v,n}$, and standard density $\rho_b$. Converges the compressibility factor K, and if necessary also the standard calorific value $H_{v,n}$, and standard density $\rho_n$, towards a final value, than the calculation of the wanted quantities is completed, because these are now directly available respectively can itself be calculated by means of the calculated values for the compressibility factor K. Is there however no convergence to be ascertained, than the result of the compressibility factor K is put back again into the input quantities of the standard-arithmetic procedure and with these changed input quantities the iteration is started once again and after passing through the steps of the procedure once again examined for convergence. Doing this beside the convergence of the value of the compressibility factor K, like this is represented in the FIGS. 2a and 2b, additionally also the convergence of the quantities evaluable from the compressibility coefficient K, for example standard calorific value $H_{v,n}$, and standard density $\rho n$ can be examined and be utilised as further criterion for termination of the iteration.

At the procedure according to FIG. 2b a first approach for the values of K and $Z_n$ is made, according to the determination of the directly with conventional means measurable quantities of the probe gas as pressure $p_b$ and temperature $T_b$ at operating conditions as well as of the evaluation of the spectrum by means of the direct spectral evaluation (DAS), which at most easy can be drawn from a characteristic diagram, that represents the influence of pressure ph at operating conditions and temperature $T_b$ at operation condition for a known composition of gas similar to the probe gas. With these quantities then for the first time according to the standard-arithmetic procedure GERG88 the respective input quantities of the respective standard-calculation procedure will be calculated and these are then used in the respective iterational procedure. As a result of this a value for the compressibility factor K is obtained as well as the here from calculatable quantities standard calorific value $H_{v,n}$, and standard density $p_n$. Converges the compressibility factor K, and if necessary also the standard calorific value $H_{v,n}$, and standard density $p_n$, towards a final value, than the calculation of the wanted quantities is completed, because these are now directly available respectively can itself be calculated by means of the calculated values for the compressibility factor K. Is there however no convergence to be ascertained, than the result of the compressibility factor K is put back again into the input quantities of the standard-arithmetic procedure GERG88 and with these changed input quantities the iteration is started once again and after passing through the steps of the procedure once again examined for convergence. Doing this beside the convergence of the value of the compressibility factor K, like this is represented in the FIGS. 2a and 2b, additionally also the convergence of the quantities evaluable from the compressibility coefficient K, for example standard calorific value $H_{v,n}$, and standard density $p_n$, can be examined and be utilized as further criterion for termination of the iteration.

At the procedure according to FIG. 2b a first approach for the values of K and $Z_n$ is made, according to the determination of the directly with conventional means measurable quantities of the probe gas as pressure $p_b$ and temperature $T_b$ at operating conditions as well as of the evaluation of the spectrum by means of the direct spectral evaluation (DAS), which at most easy can be drawn from a characteristic diagram, that represents the influence of pressure $p_b$ at operating conditions and temperature $T_b$ at operation condition for a known composition of gas similar to the probe gas. With these quantities then for the first time according to the standard-arithmetic procedure GERG8B the respective input quantities of the respective standard-calculation procedure will be calculated and these are then used in the respective iterational procedure. As a result of this a value for the compressibility factor K is obtained as well as the here from calculatable quantities standard calorific value $H_{v,n}$ and standard density $p_n$. Converges the compressibility factor K, and if necessary also the standard calorific value $H_{v,n}$ and standard density $p_n$, towards a final value, than the calculation of the wanted quantities is completed, because these are now directly available respectively can itself be calculated by means of the calculated values for the compressibility factor K. Is there however no convergence to be ascertained, than the result of the compressibility factor K is put back again into the input quantities of the standard-arithmetic procedure GERG88 and with these changed input quantities the iteration is started once again and after passing through the steps of the procedure once again examined for convergence. Doing this beside the convergence of the value of the compressibility factor K, like this is represented in the FIGS. 2a and 2b, additionally also the convergence of the quantities evaluable from the compressibility coefficient K, for example standard calorific value $H_{v,n}$ and standard density $p_n$. can be examined and be utilised as further criterion for termination of the iteration.

In the following FIGS. 4 to 10 are outlined now advantageous embodiments of the devices according to the invention. Same numerals indicate respectively identical or functionally similar devices, so that in the FIGS. 4 to 10, in essence only the differences in the respective embodiments are represented and otherwise is referred to the respective above mentioned description.

The photometric device presented in the FIG. 3a according to the state of art shows a radiation source 2, which emits spectral broadband radiation 15 in the relevant spectral area, here especial in infrared. The radiation 15 is guided through the probe gas I. that itself is located in a probe cell 3, for example in a optical measuring cell, which is chargeable by means of the orifices 4, 5. The radiation 15 is absorbed wavelength selective by the probe gas 1 corresponding of its composition of substances and the transmitted radiation 16 is fed to a modulation unit 6, that performs a spectral analysis of the transmitted radiation 16. For this, like in the FIG. 3 schematically hinted, a prism can be used, which discharges the radiation 8 of the different wavelengths in different directions. Also arrangements of gratings or the same are usual. The selective detection of a certain wavelength is achieved by positioning of a radiation sensible radiation receiver 7 along the adjustment direction 14 in the appropriate position of the spectral widened measurement radiation 8 or by way of turning the prism. A computational unit 10 registers the by means of signals 9 transmitted, detected measurement radiation 8 as a function of the wavelength and gains in this way the transmission spectrum according to FIG. 3b of the probe gas 1, that can be evaluated particularly according to the above presented procedure in respect of the wanted gas quantities. Beside the signal processing the computational unit 10 serves in addition for the control of the radiation source 2 by means of signals 11, for example for modulating of the luminous intensity, as well as for the control of the selection of the wavelength by means of signals 12 according to the movements of the prism 17 or by means of signals 13 according to the movement of the radiation receiver. The device according to FIG. 3a delivers a transmission spectrum, as for example represented in FIG. 3b, that is evaluated according to the above presented procedure in the way of MVA or in the way of DSA and will be translated by means the above presented iterational procedures to the desired standard quantities.

Figure 4:
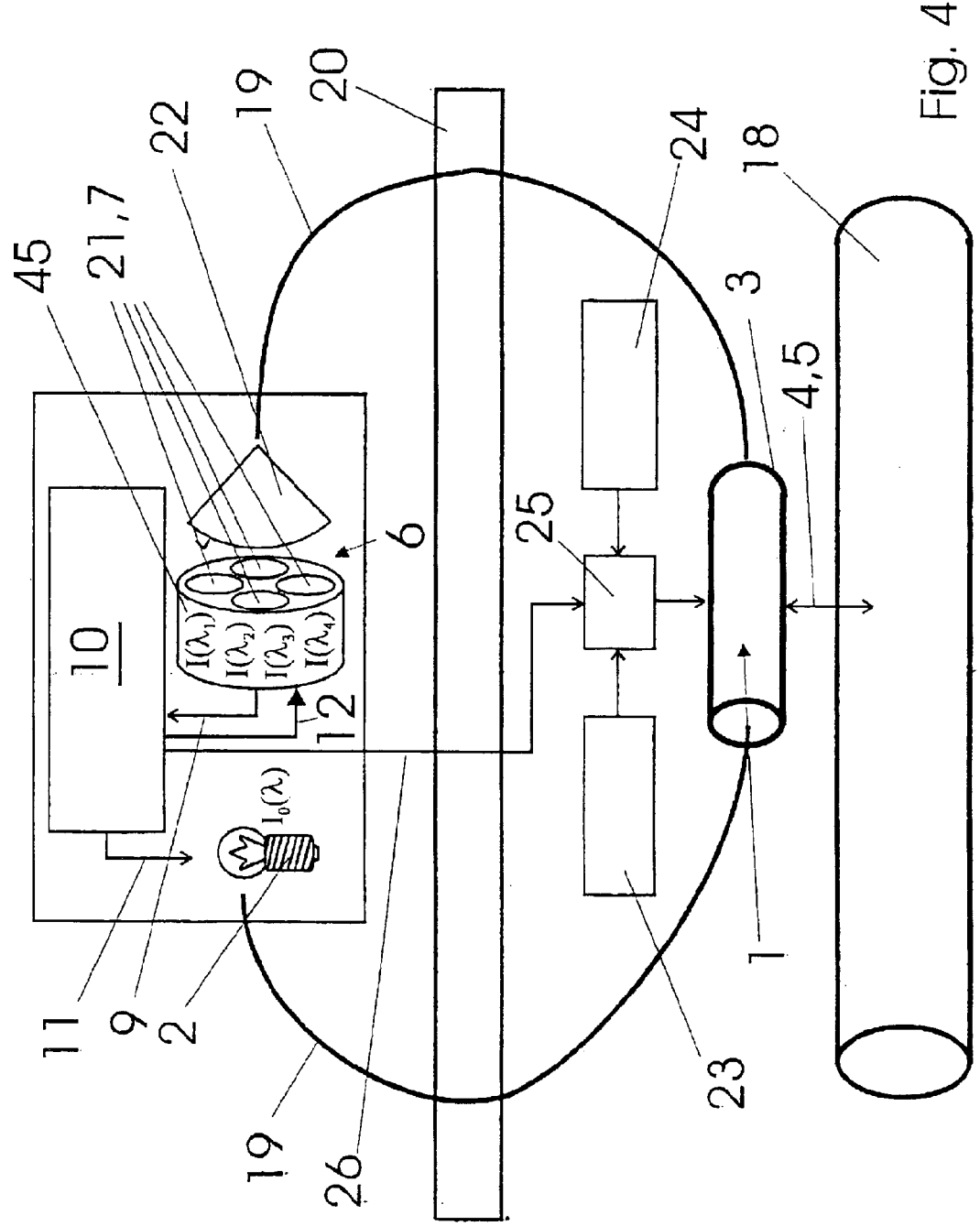

In a first conceivable embodiment of the invention FIG. 4 the device is coupled by means of optical fibres 19 to the probe cell 3 and can like this be installed in an explosion-free room behind an explosion barrier 20, while the intrinsic measuring cell itself is located near the gas conduit 18 within not explosion free room. For the recording of a null spectrum and in doing so the offset-transmission of the optical system the probe cell 3 can be filled with a spectroscopical inactive inert gas 23, in infrared for example nitrogen. Alternatively the probe cell 3 can be admitted in addition with a calibrating gas 24 for the verification of the measurement values. Null- and calibrating measurement are carried out in appropriate selected time intervals and are controlled via a valve block 25 by the computational unit 10. This embodiment can also be combined with the other implementations.

The device according to the invention registers according to FIG. 4 no spectral continuously resolved spectrum, instead uses for selection of the wavelength optical filter 21 (for example interference filter), which are positioned in front of each radiation receiver 7. Alternative also an individual radiation receiver 7 can be used, whereas the filter 21 is positioned sequentially for example by a wheel of filters 45 into the optical path of a optic 22. The filter regions are for example selected like this, that they emulate the spectral function in the above presented DSA-procedure and deliver directly the wanted quantities in operation condition. The translation to the standard quantities is done by means of the above presented two-stage iterational procedure. An especially easy assembly for the filters would be for example made of four filters: one each for $CH_4$, higher CH, $CO_2$ and reference gas.

Figure 5:
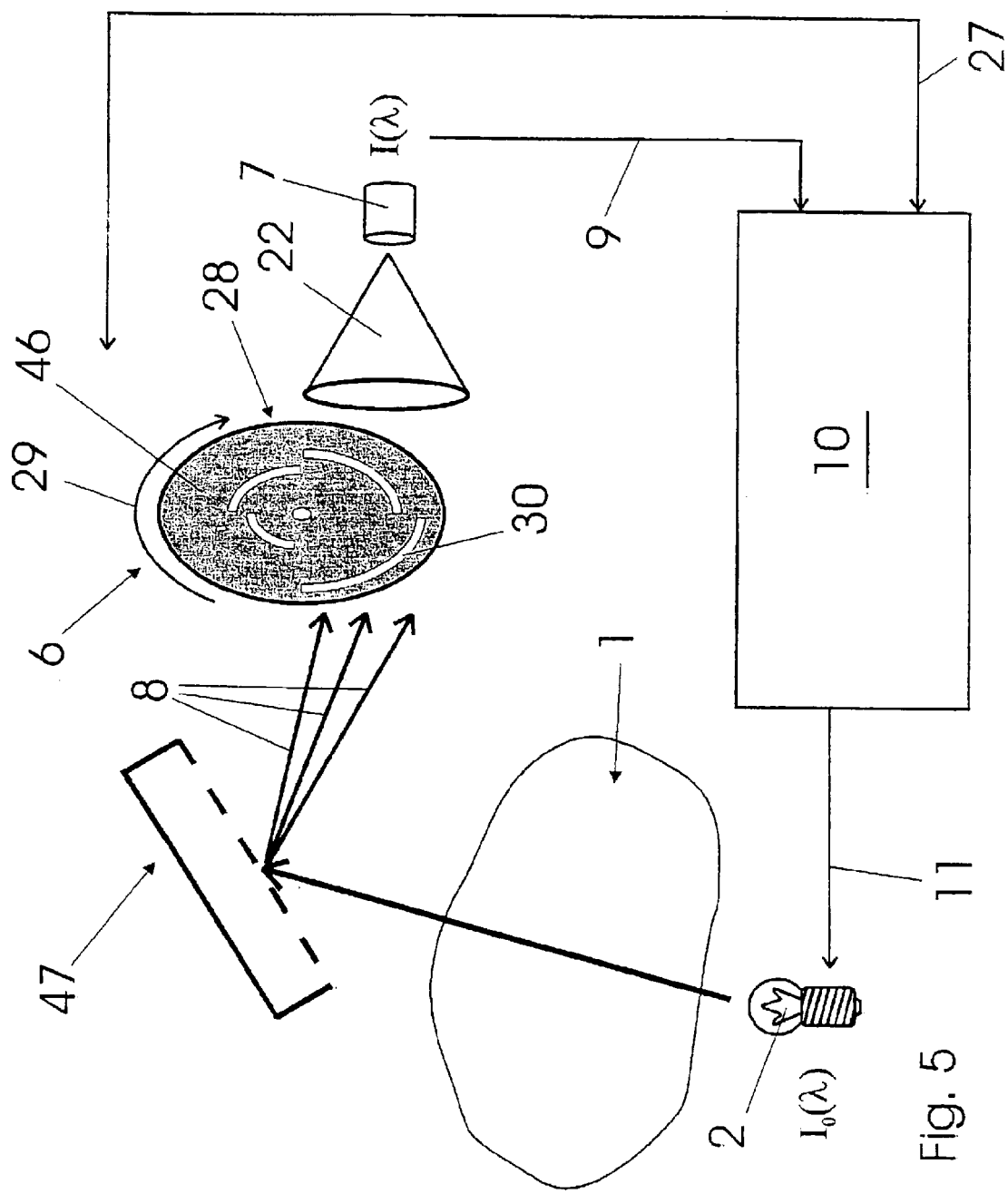
Figure 6:
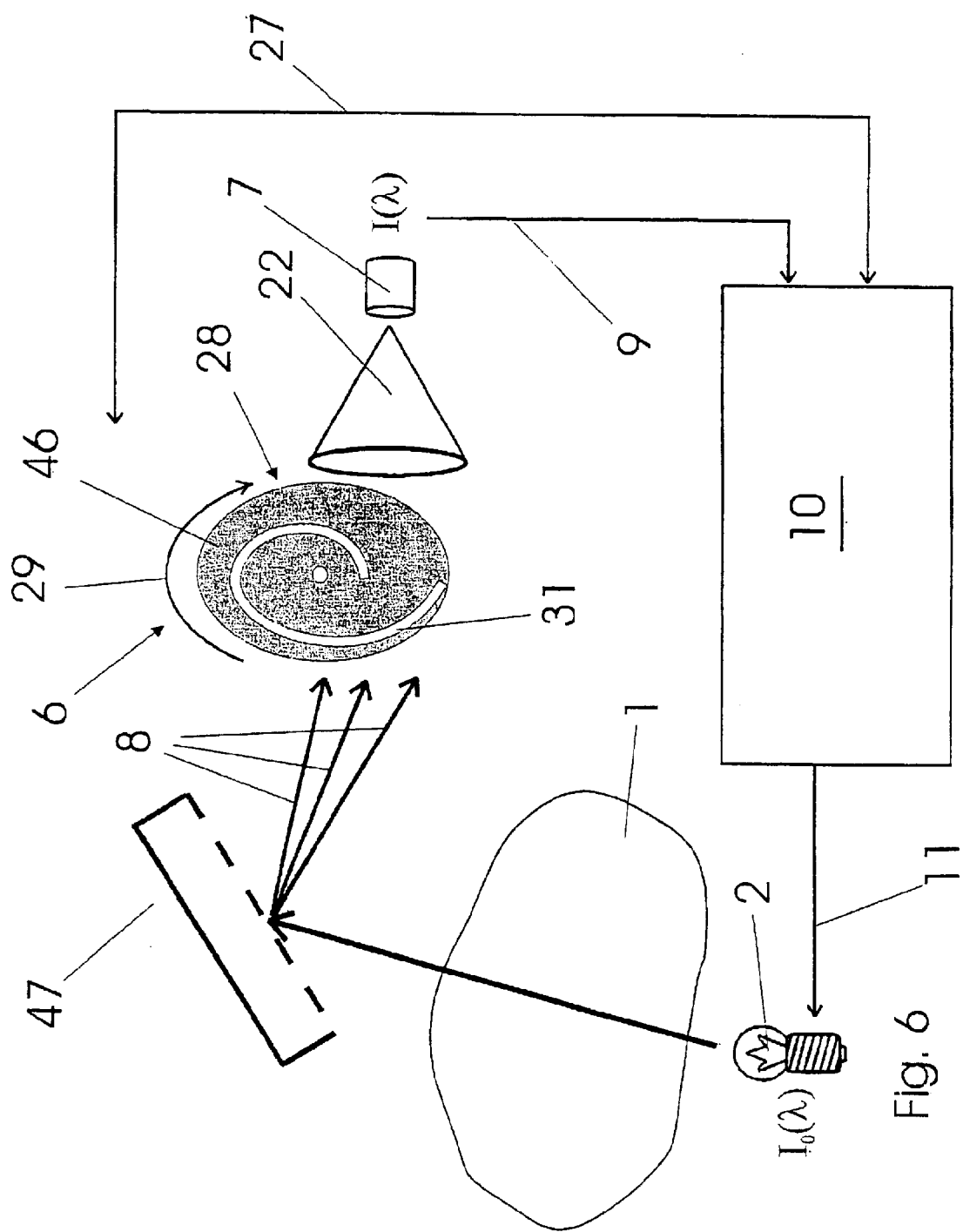

The device presented in the FIG. 5 works in combination with a prism- or grating-spectrometer, as well as provided in the embodiment according to the state of art according to FIG. 3. The selection of the wavelength is done thereby not by means of movements of a prism or of the grating or of the radiation receiver 7, instead by a in a chopper arrangement 28 provided with a sector aperture 46. This sector aperture 46 owns free sectors 30, which sequential set free areas of the outlet slit of the grating 47 or the same and with it selected regions of wavelengths of the spectrum of the measurement radiation 8. A projection lens 22 maps the transmitted measurement radiation 8 to a radiation receiver 7; based on the slit-like geometry for the projection lens 22 for example a cylindrical lens will be the best opportunity. With the information of the position of the rotational direction 29 of the rotating aperture 46 and therewith of the wavelength the computational unit 10 determines a simplified transmission spectrum, which is evaluated with the above presented procedure. By the selection of the position and width of the sectors 30 regions of wavelengths can be selected, which are optimised for the above presented evaluation procedures, particularly for DSA. The computational unit 10 controls with signals 27 also the rotational movement of the aperture 46. An alternative type design of the chopper arrangement 28 according to FIG. 5 is represented in the FIG. 6. The chopper arrangement 28 acts appropriately to sector aperture 46 of the FIG. 5, whereby however not sequential fixed wavelength intervals are faded in, instead the spectrum rather gets scanned continuously by a spiral slit opening 31 arranged in the aperture 46. The advantage is thereby a superior flexibility for the evaluation of the spectrums, however the measurement time for every interval of wavelength is shortened and in doing so the signal-noise is increased. As with the chopper arrangement 28 according to FIG. 5 the computational unit 10 ascertains based on the position of the aperture 46 the respective present wavelength and in doing so records a transmission spectrum for the above evaluation procedures MVA and DSA.

Figure 7:
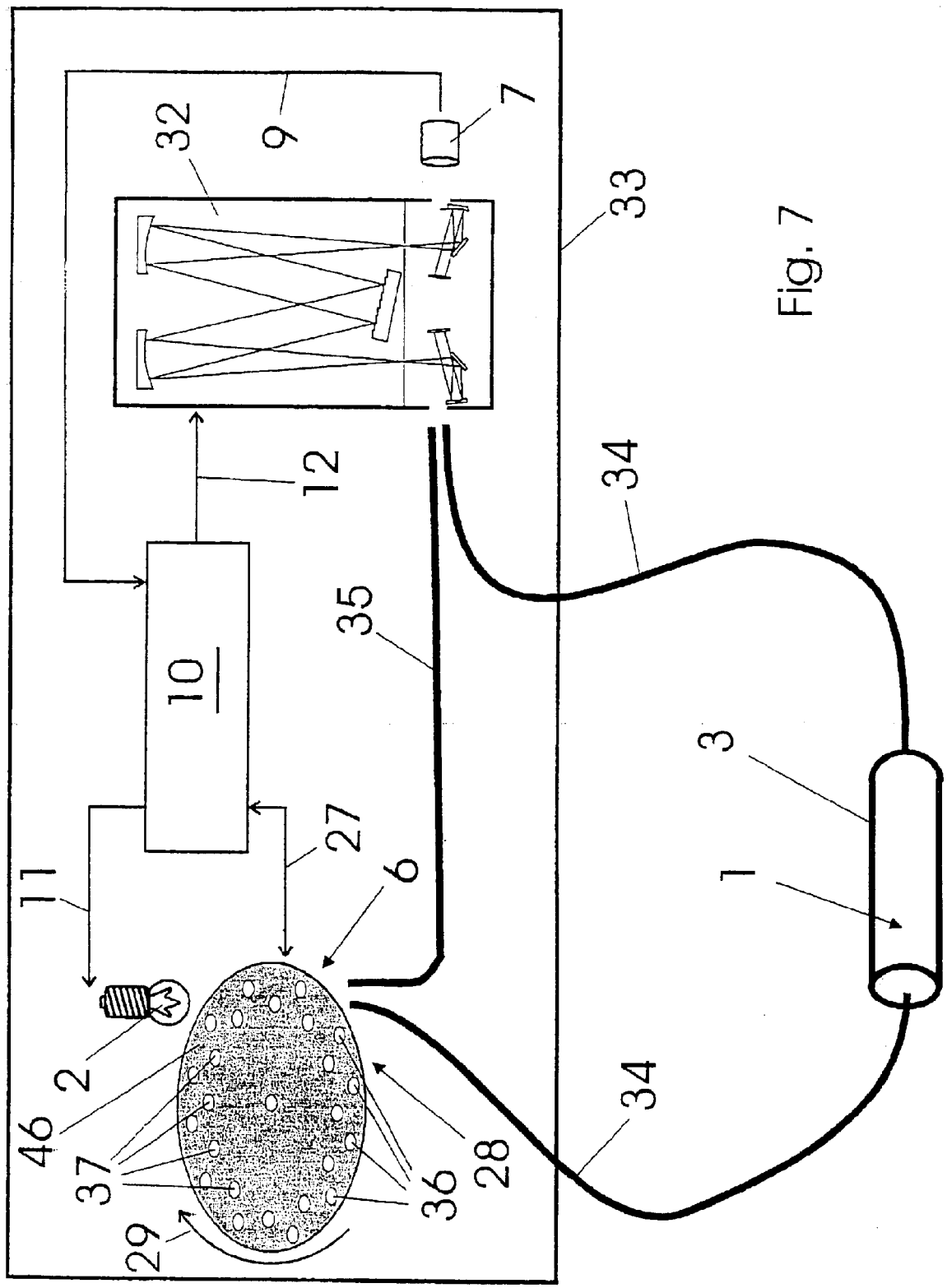

In the FIG. 7 is represented an enhanced device with a chopper arrangement 28, in which a reference channel is realised by an optical waveguide 35 for that purpose, that the open in the surrounding air guided optical path of the signals by the way of the waveguide 34 and the one of the reference beam through the waveguide 35 are identical, so that for example the underground spectrum of the atmospheric $CO_2$ as well as variances of the radiation source and the radiation receiver can be ideally suppressed. The change between the two channels in the waveguides 34, 35 is done thereby by a respective chopper arrangement 28 between radiation source 7 and coupling in of the measurement radiation 8 into the waveguides 34, 35, which illuminates by way of different sector element groups 36, 37 alternating the fibre facets of the two waveguides. The ends of the two channels of the waveguides 34, 35 are arranged closely to each other in the entrance slit of the monochromator 32, so that both fibre facets cover the same wavelength regions and a spreading of the slit and therewith a reduction of the spectral resolution is not required. The figures of the two fibre facets in the leaving slit of the monochromator 32 lie corresponding just as one upon the other and must be unified in the radiation receiver 7; this is done for example by choosing a radiation receiver 7 with a sufficiently large surface, for the sake of capturing both light spots, or by an easily defocussed adjustment of the radiation receiver 7. The intrinsic measuring apparatus can be installed doing this for example in a housing 33 encapsulated against environmental conditions.

Figure 8:
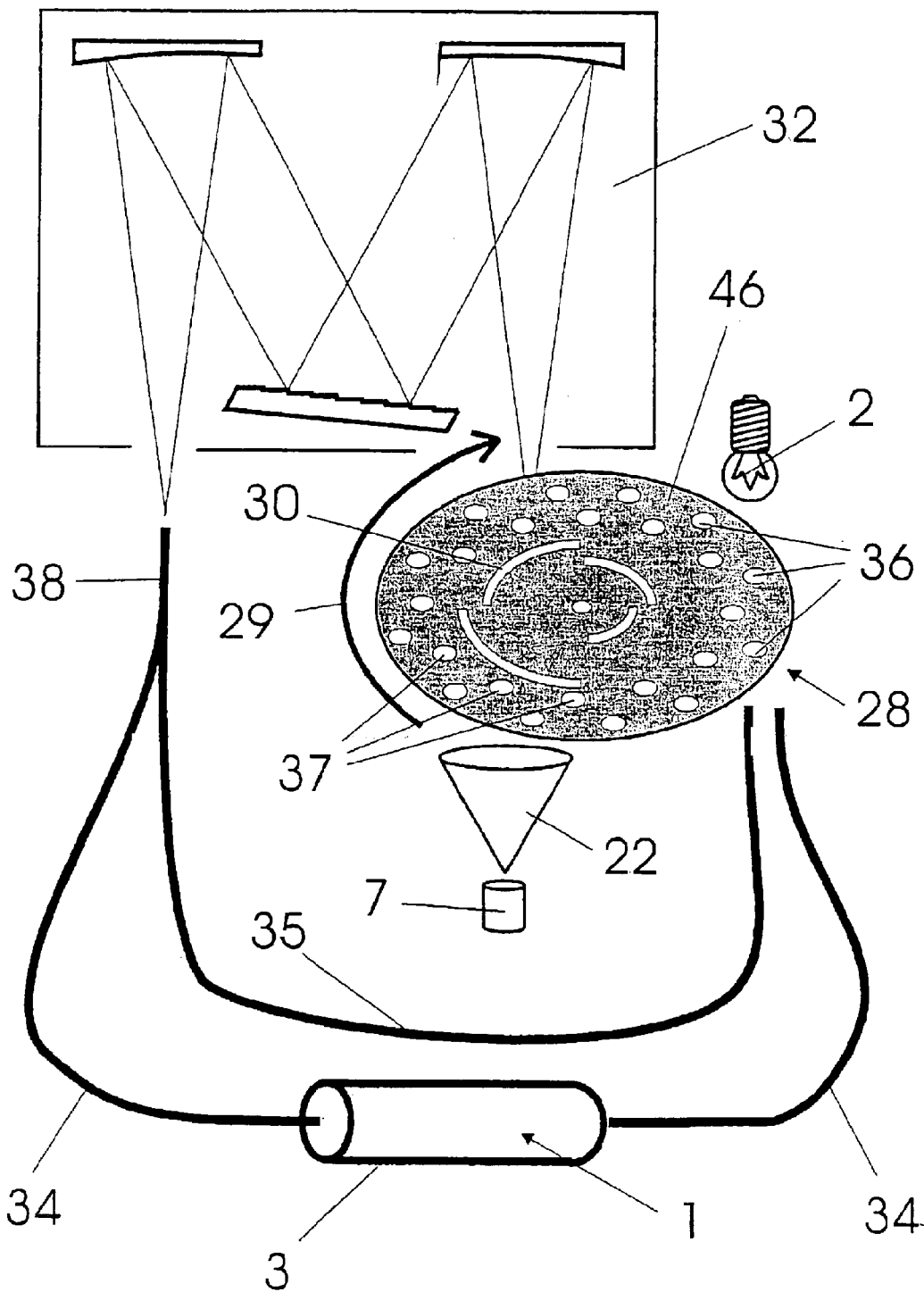

A further variant of the device according to the invention shows the FIG. 8. In this embodiment the chopper arrangement 28 simultaneously takes over two functions: on the one hand the selection of the wavelengths by means of segment openings 30 will be carried out corresponding to the embodiments according to the FIGS. 6 and 7, on the other hand the switchover between signal- and reference channel according to FIG. 7 is done by means of respective segment openings 36, 37 in the border area of this same aperture 46. The advantage of this embodiment is the compact and easy carrying out of both functions with only one drive, in addition the synchronousness of the wavelength modulation with the modulation of the beam channel is automaticly assured. In the presentation according to the FIG. 8 in addition a so-called Y-fibre coupler 38 will be used to unify the radiation of reference channel and signal channel in the entrance slit of the monochromator 32.

Figure 9:
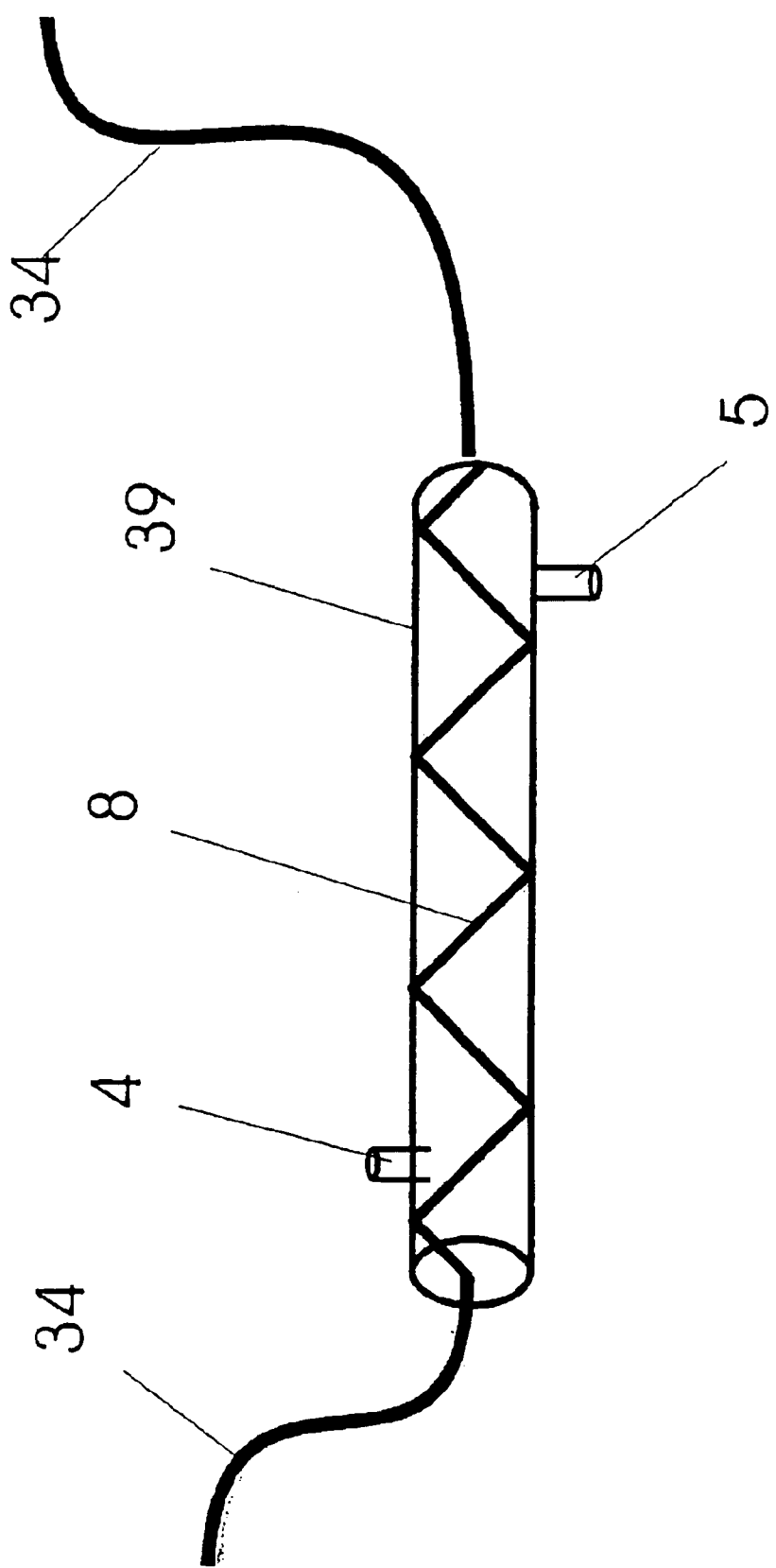
Figure 10:
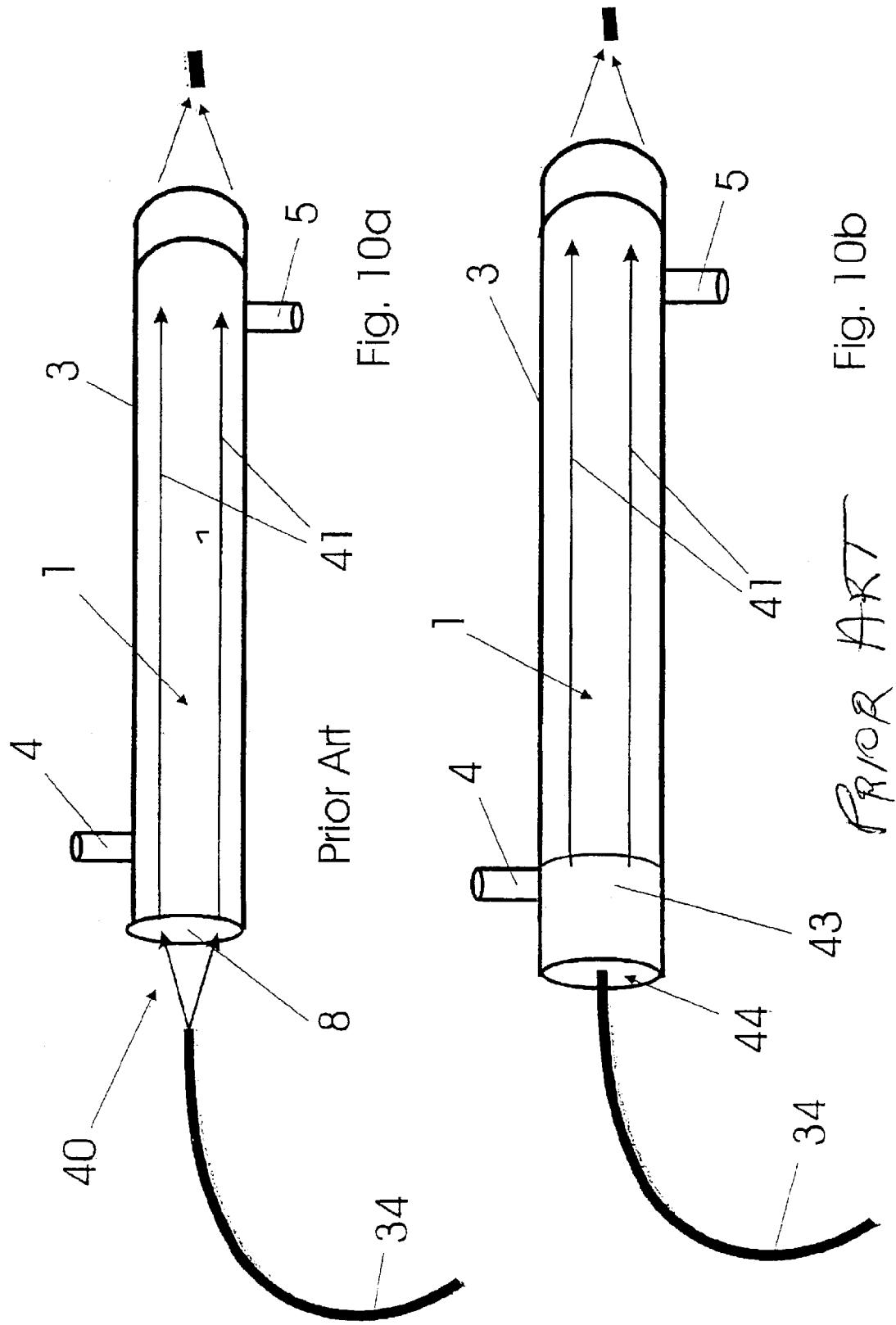

The FIG. 9 shows a design of a probe cell 3 in the shape of a hollow shaft guide 39. In optical probe cells 3 with coupling to a waveguide 34 the measurement radiation 8, which is discharged by the waveguide 34, will usually be collimated by an optic and in the form of a parallel beam guided through the probe cell 3, and is further focused with an other optic again into the waveguide 34. In FIG. 9 the probe cell 3 is realized as optical hollow shaft guide 39. An optical hollow shaft guide 39 is generally a small tube with round cross-section and an inside mirrored wall, so that the coupled-in measurement radiation 8 will be guided through multiple reflection through the hollow shaft wide 39. The dimensioning of the cross-section of the hollow shaft guide 39 is located preferably about in the size range of the waveguide 34. Hereby additional optics for coupling of waveguide 34 and hollow shaft guide 39 will be unnecessary.

The design of the probe cell 3 as hollow shaft guide 39 has thereby following advantages: The probe cell 3 can be coupled as hollow shaft guide 39 very simple and without additional optics to the supplying and the carrying away waveguide 34. The design is essentially more compact as in the case of a free guided parallel beam. The effective path length of the measured length and therefore also the sensitivity by way of the zigzag-path is improved. Because the hollow shaft guide 39 is build as a pipe, he can be connected in addition via connectors 4, 5 very good with gas conduits 18.

A further application of this optical probe cell 3 in form of a hollow shaft guide 39 can be the optical detection for gas chromatographs. The stream of gas, which escapes off the capillary column of the gas chromatograph, is directly guided through the hollow shaft guide 39 and optically determined.

The FIG. 10b shows a further improvement of the coupling of the waveguide 34 to the probe cell 3 by means of so-called. GRIND-lenses 43. In the atmospheric air are contained gases as $CO_2$ and water steam, which might disturb by their fluctuation the measuring of gas in the probe cell 3 at the state of art according to FIG. 10a; it has therefore to be avoided, that the measurement radiation 8 is guided across free optical paths 40 with surrounding air. In a spectrometer this effect will be compensated by a two-beam-concept; in the probe cell 3 however as well free paths 40 occur in the fibre optic. By using lenses with a radial gradient of refraction index. so-called GRIND-lenses 43 according to FIG. 10b the collimation and focusing can be done without free optical paths 40 and so the influence of the measurement through atmospherical air is suppressed.

Figure 11:
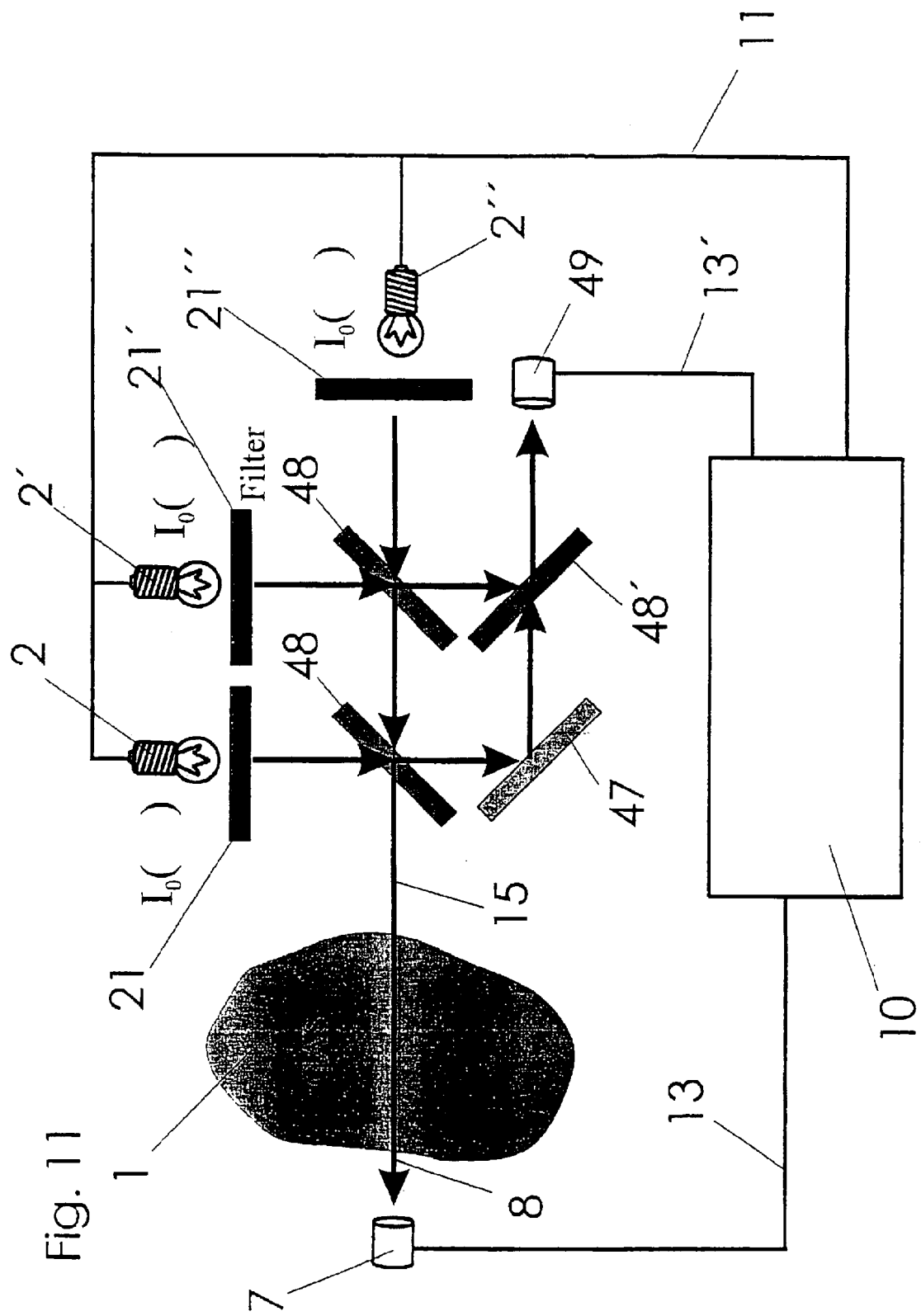

In the FIG. 11 is represented an embodiment of the invention with modulation of the measurement radiation, in which respectively for certain spectral regions of the digital signal evaluation designed filters 21, 21' and 21" respective radiation sources 2, 2' and 2" are arranged adjacent and the radiation 15 before passing through the probe gas 1 is unified through an arrangement of beam-sputters 48 for the radiation 15. Doing this the filters 21, 21' and 21" are employed in their filter behaviour in such a way, that they only let pass through spectral regions of the emitted radiation coming from the radiation sources 2, 2' and 2", which are desired for the desired spectral regions for the digital signal evaluation. After the unification of the beams of these three partial beams with the beam-splitter 48 the radiation 15 passes a not nearer described probe cell 3, in which probe gas 1 is included. The escaping measurement radiation 8 after having passed the not further described probe cell 3 will be trapped in already basically known manner by a radiation receiver 7 and reported to the computational unit 10 in also already presented manner. This computational unit 10 controls doing this both the radiation receiver 7 as well as by means of control signals 13 also the radiation sources 2, 2' and 2" by means of the control signals 11, whereby both the radiation sources 2, 2' and 2" are variable in such a manner, that a modulation of the radiation sources 2, 2' and 2" in amplitude and/or wavelength can be done. Also it is self evidentially thinkable, that an additional modulation unit can be provided, which is here however not farther represented, that modulates the measurement radiation 8 itself after leaving the radiation sources 2, 2' and 2". For stabilization of the measurements according to the FIG. 11 a further optical path is built up, by means of which partial beams coming off the beam-splitter 48 via mirrors 47 and a beam-splitter 48' shine into a reference detector 49 and there can be utilized for the compensation of unwanted effects. Also the reference detector 49 is connected via control signals 11' with the computational unit 10.

The FIGS. 4 to 11 show in a very simplified representation an equipment basic design of a device according to the invention. In this the description is restricted to the essential courses of the procedures and thereto necessary devices. It can be understood, that the expert can carry out with the teachings according to the invention according to the claims a large number of variations and adaptations, that also are covered by the item of the invention.

Parts List 1 probe gas
2,2',2" radiation source probe cell outlet
3 probe cell
4 outlet
5 intake
6 modulation unit
7 radiation receiver
8 measurement radiation
9 measurement signals
10 computational unit
11 control signals for radiation source
12 control signals for modulation unit
13,13' control signals for radiation receiver
14 movement device for radiation receiver
15 radiation in front of probe cell
16 radiation after leaving of probe cell
17 direction of movement of oscillation
18 gas supply
19 waveguide
20 explosion barrier
21 interference filter
22 projection lens
23 inertial gas
24 calibrating gas
25 valve block
26 drive for taking probes
27 control signals for chopper
28 chopper
29 direction of turning of chopper
30 opening segments of chopper
31 spiral chopper
32 monochromator
33 housing
34 first optical waveguide
35 second optical waveguide
36 first sector element group
37 second sector element group
38 Y-fibre coupler
39 hollow shaft guide
40 free path
41 parallel beam
42 spherical lens
43 grind-lens
44 direct coupling
45 filter carrier
46 aperture
47 mirror
48,48' beam-splitter
49 reference detector

What is claimed is:

1. Procedure for the determination of the quality of gas of a probe gas, proceeding from a transmission spectrum of the probe gas determined at operating conditions by means of spectroscopical methods of measurement, comprising determining at operating conditions out of the transmission spectrum the amounts of substances $x_i$ of the components of the probe gas, presetting default values for a compressibility factor K and real gas factor $Z_n$ for calculation of the compressibility factor K, out of quantities at operating conditions of the probe gas as well as from the amounts of substances $x_i$ and substance specific quantities and taking into account of the preset default values for compressibility factor K and real gas factor $Z_n$ determining input quantities for the determination of the compressibility factor K, calculating with these input quantities the compressibility factor K by means of a standard-arithmetic procedure, and carrying out an iterative calculation in the way of an iterative recalculation of the input quantities with the determined value for the compressibility factor K, until the value of the compressibility factor K converges and then from the volumetric standard calorific value $H_{v,n}$, the standard density $\rho_n$ is calculated.

2. The procedure according to claim 1, wherein as standard-arithmetic procedure the method of iteration AGA8-92DC is used.

3. The procedure according to claim 1, wherein as standard-arithmetic procedure the method of iteration GERG88 is used.

4. The procedure according to claim 1, wherein the amounts of substances $x_i$ of infrared active components of the probe gas at operating conditions is determined starting from the recorded transmission spectrum by means of multivariate analysis (MVA).

5. The procedure according to claim 1, wherein the default values of the compressibility factor K and the real gas factor $Z_n$ are taken from a characteristic diagram, that describes the influence of the pressure $p_b$ at operating conditions and the temperature $T_b$ at operating conditions for a known composition of a gas similar to the composition of the probe gas.

6. The procedure according to claim 1, wherein directly from the transmission spectrum the amounts of substances of infrared active components of the probe gas at operating conditions and the amount of nitrogen $N_2$ of the probe gas are determined as a function of the amounts of substances of the infrared active components of the probe gas.

7. The procedure according to claim 6, wherein the amount of substance of nitrogen $N_2$ and the amounts of substances of the infrared active components complements each other resulting in the total volume of the probe gas.

8. Procedure for the determination of the quality of gas of a probe gas proceeding from a transmission spectrum of the probe gas determined at operating conditions by means of spectroscopical methods of measurement, comprising, presetting default values for compressibility factor K and real gas factor $Z_n$ for calculation of the wanted compressibility factor K, from the pressure $p_b$ at operating conditions and the temperature $T_b$ at operating conditions of the probe gas with the values for the calorific value $H_{v,b}$ at operating conditions and the density $\rho_b$ at operating conditions, which can be directly determined out of the transmission spectrum, determining input quantities for the determination of the compressibility factor K, as further input quantity determining the molar amount of substance of $CO_2$ by means of a further absorption band of the transmission spectrum, with these input quantities calculating the compressibility factor K by means of the iterational procedure GERG88, carrying out an iterative calculation in the way of an iterative recalculation of the input quantities with the determined value for the compressibility factor K, until the value of the compressibility factor K converges and then from the volumetric standard calorific value $H_{v,n}$ the standard density $\rho_n$ is calculated.

9. The procedure according to claim 8, wherein the calorific value $H_{v,b}$ at operating conditions and the density $\rho_b$ at operating conditions are determined by means of spectral functions for weighting of a value directly from the transmission spectrum of the probe gas.

10. The procedure according to claim 9, wherein with the spectral functions for weighting of a value the weighted influence of the amounts of substances of the components of the probe gas is described for the calorific value $H_{v,b}$ at operating conditions and the density at operating conditions.

11. The procedure according to claim 9, wherein the default values for compressibility factor K and real gas factor $Z_n$ are taken from a characteristic diagram, that describes the influence of the pressure $p_b$ at operating conditions and the temperature $T_b$ at operating conditions for a known composition of a gas similar to the composition of the probe gas.

12. Photometric device for the determination of a transmission spectrum of a probe gas comprising a radiation source emitting a measurement radiation, in which the measurement radiation passes through a probe cell for capturing a probe gas and enters after passing through a modulation unit for modulating the measurement radiation into at least one radiation receiver, which generates electrical measurement signals according to an incoming intensity of the measurement radiation and transmits these to an electronic unit, which determines said transmission spectrum out of the measurement signals, wherein the modulation unit shows a spectral switch unit in the form of a chopper arrangement, which transmits because of their selective transmission behaviour only specific spectral regions of the transmission spectrum in the measurement radiation caused by the probe gas to the at least one radiation receiver; and wherein the chopper arrangement is provided with an aperture with a spiral opening in which the release of the regions of the wavelength of the measurement radiation is caused continuously for the whole spectrum.

13. The photometric device according to claim 12, wherein the chopper arrangement provides such a transmission spectrum that the transmitted specific spectral regions are suitable for the further evaluation by procedures of the direct spectral evaluation (DSA).

14. The photometric device according to claim 12, wherein the release of the regions of the wavelength of the measurement radiation, which passes through the chopper arrangement, can be obtained by means of capturing the rotational position of the aperture.

15. The photometric device according to claim 12, wherein the chopper arrangement is provided with two groups of sector elements alternatively releasing the measurement radiation, in which a first optical waveguide guides the measurement radiation released by the sector elements of the first sector element group into the probe cell and after passing through the probe cell to the at least one radiation receiver and a second optical waveguide guides the measurement radiation released by the sector elements of the second sector element group directly to the at least one radiation receiver.

16. The photometric device according to claim 15, wherein the measurement radiation released by the sector elements of the first and second sector element groups are concentrated by means of said first optical waveguide and said second optical waveguide into one or more filters or a dispersive element, or a monochromator.

17. The photometric device according to claim 16, wherein the at least one radiation receiver collects the measurement radiation, which is coming out of the one or more filters or the dispersive element and each released through the sector elements of the sector element groups of both optical waveguides.

18. The photometric device according to claim 16, wherein the measurement radiation, which is each released through the sector elements, is guided together by means of the first and the second optical waveguides in a Y-fibre coupler, which guides the measurement radiation of the first and the second optical waveguides to the one or more filters or the dispersive element.

19. The photometric device according to claim 15, wherein the measurement radiation, which is released through the sector elements of the sector element groups of that first optical waveguide, which is guided directly to the at least one radiation receiver, is usable as reference for eliminating the influence of $CO_2$, which exists in the surrounding of the probe cell and/or of the photometric device, of changes of the radiation source and/or of the at least one radiation receiver.

20. The photometric device according to claim 15, wherein the measurement radiation, which is each released through the sector elements of the first and second sector element groups, is guided through the first and the second optical waveguide to the input of one or more filters or a dispersive element, in which at the chopper arrangement also available sector element groups lock on the measurement radiation, which is released of the one or more filters or the dispersive element, alternatively to the at least one radiation receiver.

21. The photometric device according to claim 20, wherein the chopper arrangement carries out both the selection of the wavelengths for the transmission spectrum as well as the alternating of the measured section of measurement radiation between the first and second optical waveguides.

22. The photometric device according to claim 15, wherein the probe cell is sweepable with an infrared inactive gas, for the compensation of dirt accumulation of the optical facilities of the photometric device.

* * * * *